United States Patent [19]

Crum

[11] Patent Number: 5,027,819

[45] Date of Patent: Jul. 2, 1991

[54] MEASUREMENT OF VISUALLY INDUCED BIOMAGNETIC RESPONSES

[75] Inventor: Duane B. Crum, San Diego, Calif.

[73] Assignee: Biomagnetic Technologies, Inc., San Diego, Calif.

[21] Appl. No.: 551,882

[22] Filed: Jul. 12, 1990

[51] Int. Cl.$^5$ .............................................. A61B 5/05
[52] U.S. Cl. .................. 128/653 R; 128/901; 324/225; 324/244
[58] Field of Search ................. 128/653 R, 901, 905, 128/908, 653 A, 653 SC; 324/225, 244, 248

[56] References Cited

U.S. PATENT DOCUMENTS 3,311,821  3/1967  Brunel ................................. 324/244

FOREIGN PATENT DOCUMENTS 8807834  10/1988  PCT Int'l Appl. ............. 128/653 R Primary Examiner—Ruth S. Smith
Attorney, Agent, or Firm—Gregory O. Garmong

[57] ABSTRACT

A biomagnetometer measures the magnetic field produced by the brain as a result of a visual stimulus delivered by a display device such as a cathode ray tube (CRT). The output signal of the biomagnetometer is filtered to remove noise introduced by the operation of the display device itself, such as the repetitive scan signal of the CRT, and the CRT monitor is otherwise operated from DC power to minimize periodic variations that can interfere with the detection of brain signals. The filtering is preferably accomplished using a comb-notch filter. Cancellation coils and shielding are also preferably used to remove a portion of the noise introduced by the display device.

20 Claims, 4 Drawing Sheets

MEASUREMENT OF VISUALLY INDUCED BIOMAGNETIC RESPONSES

BACKGROUND OF THE INVENTION

This invention relates to the measurement of magnetic signals produced by the brain, and, more particularly, to measurement of visually induced responses of the brain.

The biomagnetometer is an instrument that has been developed for measuring magnetic fields produced by the body, particularly the brain. The biomagnetometer is necessarily a very sensitive measurement instrument, because the magnetic fields produced by the brain are small. The strength of the magnetic field produced by the brain is typically about 0.000000001 Gauss, at a distance of 1-2 centimeters from the head. By comparison, the strength of the earth's magnetic field is about 0.5 Gauss, or about five hundred million times larger than the strength of the magnetic field of the brain, as measured externally to the head.

The biomagnetometer includes a magnetic pickup coil connected to a very sensitive detector of magnetic signals. The currently most widely used detector is a Superconducting QUantum Interference Device or SQUID, which, in combination with a superconducting pickup coil, is sufficiently sensitive to detect magnetic signals produced by the brain. The detector, pickup coil, and their associated equipment require special operating conditions such as a cryogenic dewar, and cannot be placed into the body or attached directly to the surface of the body. The dewar is operated with its interior at liquid helium temperature (about 4.2K), to maintain the SQUID detector, the pickup coil, and the electrical connection between them in the superconducting state because of the small electrical currents involved, and to reduce the electrical noise that might otherwise influence the SQUID detector.

Special electronics is provided to filter out external effects such as the earth's magnetic field and other electrical sources. The subject and the detector can be placed into a magnetically quiet enclosure that shields the subject and the detector from the external magnetic fields. With these special provisions, medical researchers and doctors can now make accurate, reliable measurements of the magnetic fields produced by the brain in response to external stimuli.

One of the difficult problems in performing measurements of responses to visual stimuli is delivery of those stimuli to the eyes of the subject in a manner that does not, in itself, cause a signal in the biomagnetometer that interferes with its operation, obscures the responses of the subject, or is subject to misinterpretation as a response of the subject. Most electrical equipment produces magnetic fields, in many cases much larger than that of the earth's field or any brain signal that might result. A device to deliver visual stimuli to the subject under study is most conventionally placed in close proximity to the subject. Where a magnetically shielded enclosure is used, it is desirable to place the device inside the enclosure.

There is a need for a visual stimulation device that is magnetically quiet in the sense that it does not produce signals in the biomagnetometer that interfere with its operation or with the interpretation of the subject's response. The device should also be sufficiently versatile to deliver a variety of visual stimuli in an otherwise uniform manner, so that the effects of such different types of stimuli can be evaluated. The present invention fulfills these needs, and further provides related advantages.

SUMMARY OF THE INVENTION

The present invention provides an apparatus and process for delivering visual stimuli to a subject and then studying the biomagnetic response of the subject. The portion of the system that delivers the visual stimulus does not produce a signal that interferes with the biomagnetometer's operation or the interpretation of the subject's response. The apparatus is highly versatile, so that a wide range of types of stimuli can be delivered. The apparatus can be used in conjunction with a magnetically shielded enclosure of conventional design.

In accordance with the invention, apparatus for performing biomagnetic measurements of visually stimulated responses in a subject comprises means for detecting biomagnetic signals produced by a subject and having an output signal indicative of the biomagnetic signals; means for producing a visual image responsive to an electrical signal, the means for producing being disposed for viewing by the subject and in sufficient proximity to the subject that magnetic interference emitted by the means for producing is detected by the means for detecting and becomes mixed with the output signal of the means for detecting; and means for reducing the effect of the magnetic interference produced by the means for producing on the output signal of the means for detecting.

In accordance with a process aspect of the invention, a process for detecting biomagnetic signals resulting from visually induced responses in a subject comprises the steps of providing a visual image to a subject on a display device that produces a magnetic field as it operates; detecting the magnetic field produced by the subject responsive to the visual signal and the magnetic field produced by the display device as it operates, and generating an output signal indicative of the detected magnetic fields; and reducing the magnitude of those portions of the output signal resulting from the magnetic field produced by the display device.

The means for producing a visual image is preferably a cathode ray tube (CRT), which, like a television screen, is inherently capable of delivering a wide variety of visual images. However, it was found that the operation of the CRT introduces an unacceptable component to the biomagnetic output signal that is not readily filtered using the standard approaches. One component of the signal induced by the CRT originates in the deflection coils of the electron beam gun of the CRT, whose operation is responsive to its repetitive electrical synchronization signal. A satisfactory solution was therefore found by shielding, cancelling, and/or filtering those portions of the output signal of the biomagnetometer resulting from the synchronization signal. Additionally, the basic 60 Hertz alternating current electrical power for the monitor is preferably replaced by direct current (DC) power, which generates no fluctuating magnetic field of its own. It is preferable that all three techniques, shielding, cancelling, and filtering, be used to attenuate the portion of the signal produced by the display device itself. Cancellation coils and shielding are provided to reduce that undesirable portion of the signal as much as possible, but usually at least some small portion remains for removal by filtering.

Only the portion of the signal that is directly caused by the display device and is not a response of the subject, and is within some frequency range of interest, must be filtered out. It may be necessary only to filter at some of the group of fundamental and harmonic frequencies of the synchronization signal, as may be done with any number of well-known single frequency notch filters. There exists a commercially available filter termed a comb-notch filter that removes those portions of the frequency spectrum of a signal at the fundamental frequency and the harmonic frequencies of a control signal provided to the filter.

The present approach permits a CRT-based monitor or other electrical display device to be placed adjacent a subject whose response to visual stimuli is being studied. Both the subject and the monitor may be placed within a magnetically shielded room. The portion of the signal produced by the display device and detected by the biomagnetometer is reduced by shielding and field cancellation techniques, and the output signal of the biomagnetometer is filtered to remove the portion that is detected from the monitor. The filtered output signal of the biomagnetometer therefore includes only the response of the subject to the visual stimuli. Many different types of visual stimuli can be introduced through the display device, so that the response to each may be recorded and isolated. Other features and advantages of the invention will be apparent from the following more detailed description of the preferred embodiment, taken in conjunction with the accompanying drawings, which illustrate, by way of example, the principles of the invention.

DETAILED DESCRIPTION OF THE PREFERRED EMBODIMENT

In accordance with the invention, apparatus for performing biomagnetic measurements of visually stimulated responses in a subject comprises a biomagnetometer having an output signal, the biomagnetometer being disposed to detect magnetic fields produced by a subject; a signal generator that generates a repetitive electrical synchronization signal; a display device responsive to the repetitive electrical synchronization signal received from the signal generator, the display device being disposed for viewing by the subject and sufficiently close to the subject that a magnetic field produced by the display device as a result of the repetitive synchronization signal is detected by the biomagnetometer; magnetic shielding means at least partially surrounding the display device for reducing the portion of the magnetic field sensed by the biomagnetometer that is produced by the display device; magnetic field cancellation means for cancelling at least a portion of the magnetic field produced by the display device; a magnetically shielded enclosure in which the subject, the display device, the magnetic shielding means, the magnetic field cancellation means, and the biomagnetometer are located; and means for filtering from the output signal of the biomagnetometer those portions of the output signal resulting from the operation of the display device.

Figure 1:
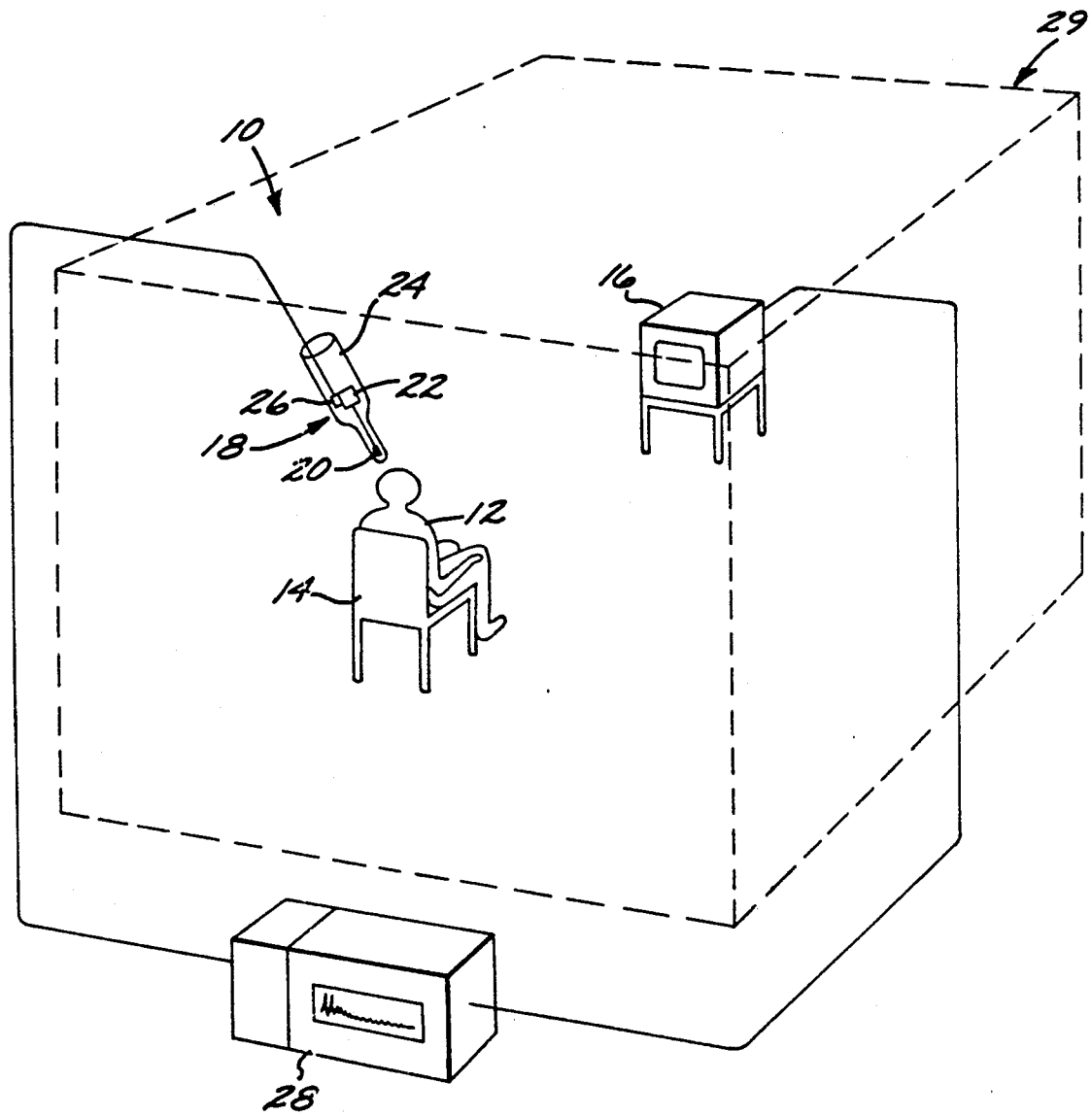
FIG. 1 is a perspective view of the interior of a magnetically shielded room, with a subject being studied using the approach of the invention.

FIG. 1 illustrates an apparatus 10 that is used to perform biomagnetic measurements of visually stimulated responses of a subject 12. In this preferred form, the subject is placed into a chair 14 facing a display device 16. The display 16 includes a cathode ray tube (CRT) and associated electronic components to display images generated remotely. Generally, the display 16 can include a CRT or any other device for presenting visual stimuli that creates a magnetic signal that may undesirably interfere with the biomagnetic measurements. Such a device normally requires electrical signals of several types. One is a repetitive electrical signal used for signal synchronization, and this signal will be discussed in detail subsequently. Another is a power signal that provides power to the display 16 to produce high voltages, operate heaters, etc. That power signal normally is 60 Hz (Hertz) AC line current, which can produce adverse electromagnetic signals. The power line signal is a periodic signal that can be filtered in the same manner as will be described for the repetitive synchronization signal. However, in the presently preferred approach the alternating line current is replaced by direct current power to the display 16, which does not produce an electromagnetic effect on the biomagnetic signals. (If the monitor is operated from conventional alternating current power, a less preferred approach, then a second filter of the type to be described subsequently may be provided, to remove periodic interference produced responsive to the power signal as distinct from the image synchronization signal.)

The detector portion of a biomagnetometer 18 is disposed adjacent the head of the subject 12. The biomagnetometer 18 includes a field coil 20 that produces a small electrical signal responsive to magnetic flux changes sensed by the coil, and a superconducting quantum interference device ("SQUID") 22 that detects the small electrical signal. The field coil 20 and SQUID 22 are placed into a dewar 24 maintained at liquid helium temperature (4.2K). The SQUID 22 is supported by cryogenic electronic circuitry 26 within the dewar 24, and additional room temperature SQUID electronic circuitry 28. All of these elements, except for the circuitry 28, are placed within a magnetically shielded enclosure 29, in the preferred approach.

The general structure of the biomagnetometer 18, including the field coil 20, the SQUID 22, and the electronics 26 and 28 are known in the art, and are described, for example, in U.S. Pat. Nos. 4,793,355, 3,980,076, 4,389,612, and 4,079,730, whose disclosures are incorporated by reference. The structure of the dewar 24 is disclosed in U.S. Pat. No. 4,773,952, whose disclosure is incorporated by reference. The structure and preparation of SQUIDs 22 is disclosed in U.S. Pat. No. 4,386,361 and U.S. Pat. No. 4,403,189, whose disclosures are incorporated by reference. The structure of a magnetically shielded enclosure 29 is disclosed in U.S. Pat. No. 3,557,777, whose disclosure is incorporated by reference.

Figure 2:
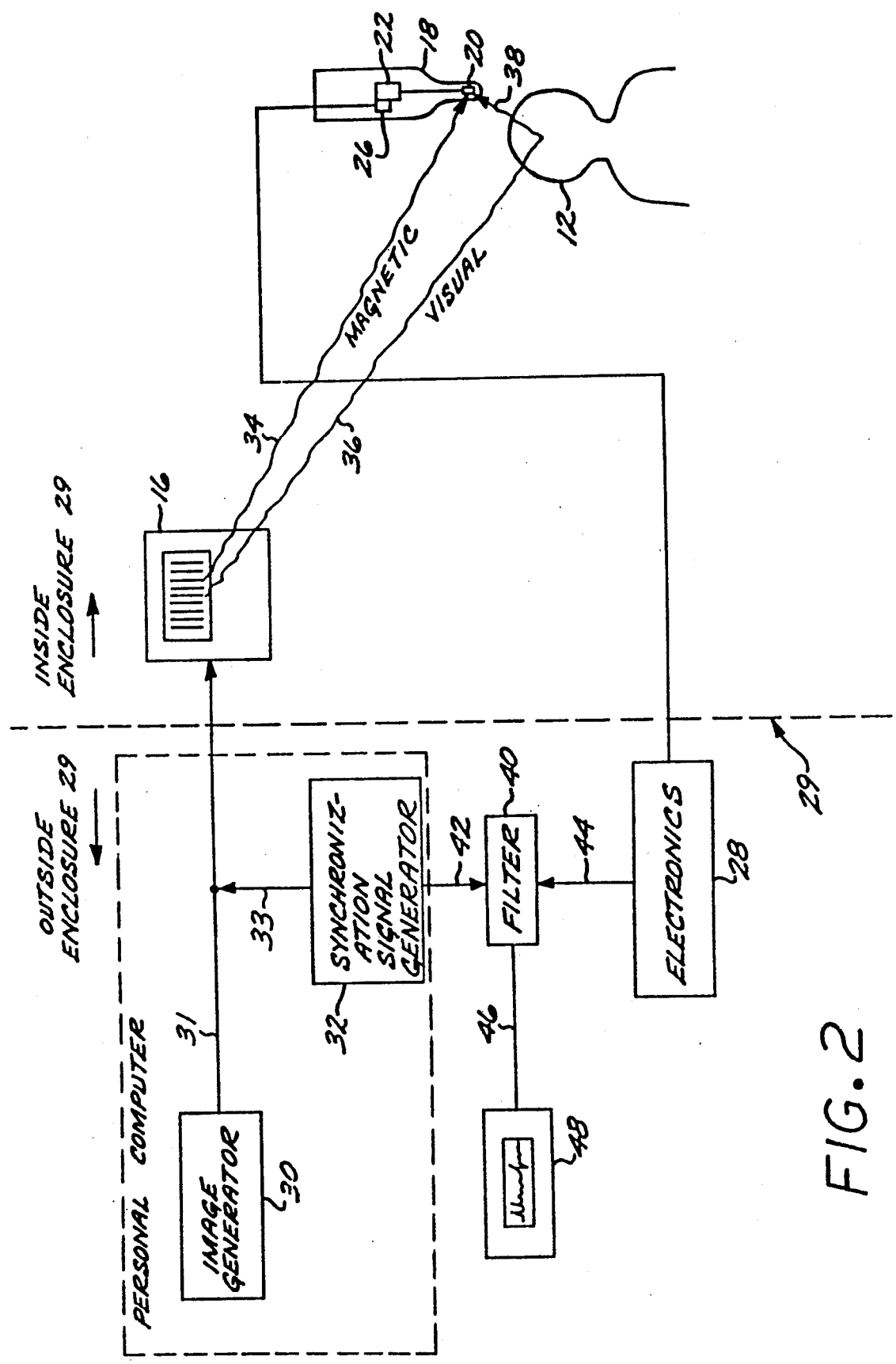
FIG. 2 is a block diagram of the electronics arrangement of the approach of the invention.

The structure and operation of a CRT-based display 16 are generally well known. Such displays are widely used, as for example in the video display terminal of word processors and small computers. As illustrated in FIG. 2, an image signal 31 is produced by any appropriate technique, such as an image generator 30 within a programmed microcomputer. Because the image is formed as a succession of frames made up of lines on the CRT, a synchronization signal 33 is generated by a synchronization signal generator 32 and mixed with the image signal 31, the mixed signal being fed to the display 16. A scan generator (not shown) in the display 16 operates deflection coils (not shown) to deflect the electron beam of the CRT to form an image on its screen.

This aspect of the procedure is identical to the manner in which images generated by a personal computer are displayed on a CRT display, and is therefore well known. Here, the personal computer is programmed to generate images that are selected by an investigator who seeks to understand their effect on the subject 12. In a presently preferred form of the present invention, the display 16 is a CRT display unit from a Commodore personal computer, and the image generator 30 and synchronization signal generator 32 are within a personal computer, here an Apple personal computer. The image generator 30 produces an image selected by a human investigator, and that image is transmitted to the display 16. The synchronization signal is mixed into the image signal at appropriate locations, so that the display 16 displays frames of information on its CRT screen.

Figure 3:
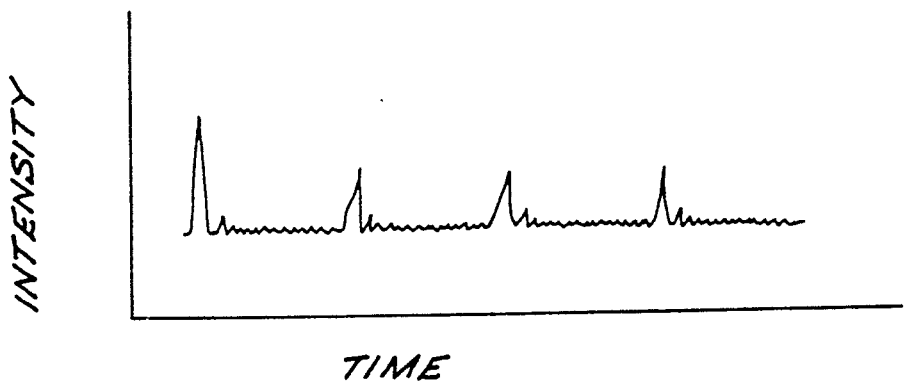
FIG. 3 is a graph of an unfiltered output signal as a function of time.

In initial studies, it was found that the display 16 emits magnetic fields of sufficient magnitude that they are detected by the biomagnetometer 18. It was not possible to clearly separate the signal emitted by the display 16 from the responsive signal produced from the body of the subject 12. As depicted in FIG. 2, the display 16 produces a magnetic field 34 that is detected by the biomagnetometer 18. A visual stimulus 36 in the form of an image is viewed by the subject 12, whose brain in turn produces a magnetic field 38 that is also detected by the biomagnetometer 18. It is the subject response biomagnetic signal 38 that is of interest, not the display magnetic field 34. In the initial studies, it was not possible to clearly separate the two magnetic fields 34 and 38, both of which were detected by the biomagnetometer 18 and its SQUID 22. These mixed signals 34 and 38 were amplified by the electronics 26 and 28, producing a mixed output signal in the form shown in FIG. 3. The output signal of FIG. 3 is dominated by large peaks that have been shown to result from the undesirable magnetic signal 34 produced by the display device 16, which peaks tend to obscure the signal resulting from the subject's response 38.

To reduce and preferably remove the undesired effects of the signal 34, the mixed signal is filtered by a filter that uses a synchronization signal 42 from the synchronization signal generator 32 as a reference for the filter. Where analog filtering is used, the filter is preferably a comb-notch filter 40. The comb-notch filter 40 removes the fundamental frequency of the control signal 42, as well as the harmonic frequencies of the control signal 42, from a processed signal, here an unfiltered output signal 44. The result is a filtered output signal 46, which may be viewed on a display device 48. Comb-notch filters 40 are widely available in the industry.

Figure 4:
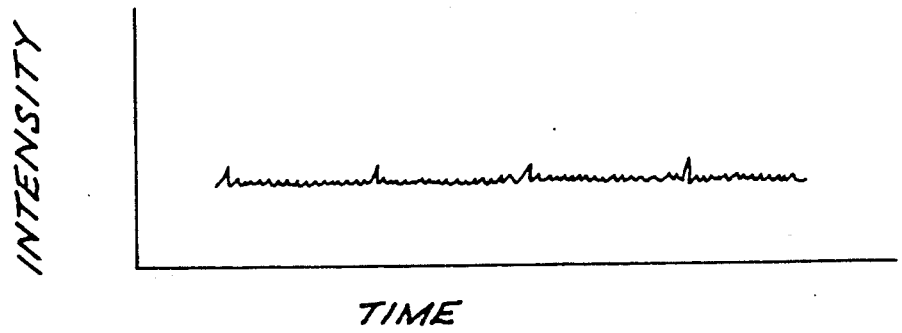
FIG. 4 is a graph of the output signal of FIG. 3, after reduction of the unwanted signal produced by the display device.

An example of a filtered output 46 is illustrated in FIG. 4. The filtered output 46 of FIG. 4 is similar to the unfiltered output 44 of FIG. 3, except that the filtered frequencies that result from the operation of the display device are removed from the filtered output 46.

Alternatively, the filter 40 may be another type of analog filter such as one or more narrow-band notch filters or a digital filter. In the case of a digital filter, the biomagnetic signal is digitized, and those portions of the digital signal caused by the display-produced interference are attenuated. As an aid in reducing the interference, the signature of the interference may be measured by the biomagnetometer in the absence of a subject, and then the digitized signal measured with a subject present is processed by subtracting the interference signature. The synchronization signal can also be digitized and supplied for use by the digital filter as is done for the analog comb-notch filter. The processing can be done by the same computer that generates the images, or a separate microprocessor. The digital filtering could be performed either on-line or off-line, after the data is gathered from the subject.

A key to the present invention is the discovery that the signal 34 emitted by the display 16 is found primarily at the fundamental frequency of the synchronization signal 32 and its harmonic frequencies. The filter 40 therefore removes that portion of the unfiltered signal 44 at a fundamental frequency, the second harmonic, and higher harmonics. The resulting filtered output signal 46 loses some small portion of the response 38 within each narrow filtered band, but if necessary even this information can be determined by changing the frequency of the synchronization so that the filtered frequencies are shifted. However, in most instances the width of the filtered bands is less than 0.1 Hz, and therefore the small loss is acceptable.

Figure 5:
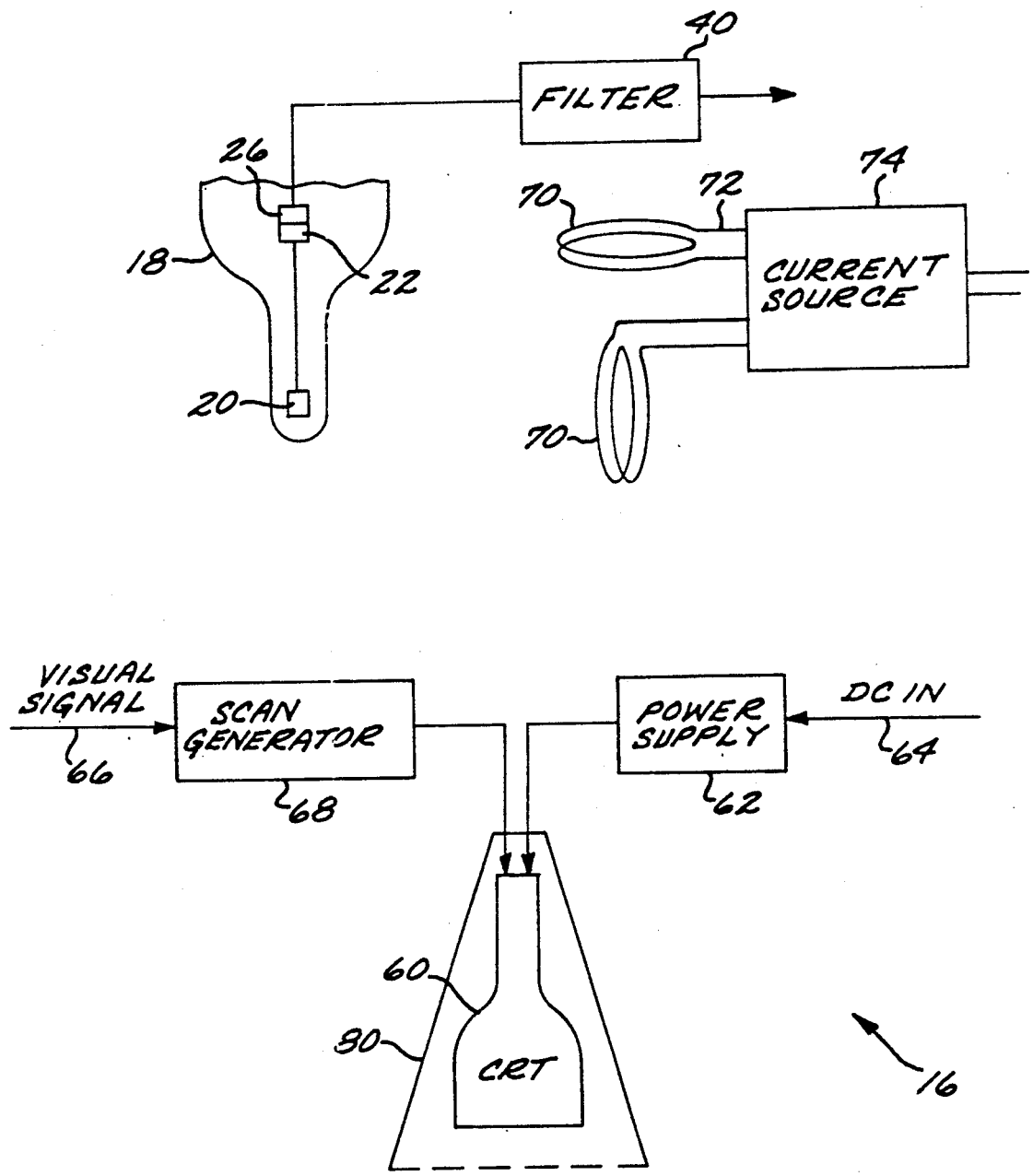
FIG. 5 is a schematic layout of a CRT with magnetic cancellation coils and shielding.

A further aid to electromagnetic noise reduction that may be employed as necessary is depicted in FIG. 5. In this approach, magnetic cancellation coils are used to partially negate the adverse effects of the noise produced by the repetitive synchronization signal. FIG. 5 depicts the interior of the display 16 in schematic form, together with the pertinent portion of the biomagnetometer 18. The display 16 includes a cathode ray tube 60, which is powered by a voltage source 62 that, in the preferred approach, is supplied by an external direct current 64. The information to be displayed on the cathode ray tube 60 is externally supplied as the mixed information/synchronization signal 66, discussed previously. The signal 66 is provided to a conventional scan generator 68, which produces x-axis and y-axis control signals that are supplied to the deflection coils of the cathode ray tube 60.

Three electromagnetic cancellation coil sets 70 are disposed within the enclosure 29 and near the foregoing components to cancel the three orthogonal magnetic field components radiated by the display. (Only two sets are shown in the two-dimensional view of FIG. 5.)

The leads 72 to the coil sets 70 are conducted out of the magnetically shielded enclosure 29 to an external current source 74. The source 74 supplies a signal to each of the coil sets 70 to at least partially cancel the portion of the electromagnetic signal 34 produced by the components within the display 16, that is otherwise detected by the biomagnetometer. Preferably, the current source 74 is controlled by measuring the output of the biomagnetometer, and then adjusting the current in the cancellation coils 70 to null out this signal. Conceivably, one precisely oriented cancellation coil could be used to null out the magnetic field emitted by the display, but three orthogonal coil sets are more practical to utilize in a commercial apparatus.

Another technique to reduce the magnitude of the magnetic field emitted by the display is to shield it with a magnetic shielding material. As illustrated in FIG. 5, a shield 80 may be placed around the CRT 60. In this case, the shield 80 is in the form of a hollow frustum of a cone, with an open narrow end to permit electrical access to the back end of the CRT 60, and an open large end to permit the subject to view the screen of the CRT 60. Preferred shielding materials have high permeability and high electrical conductivity. Preferred materials include mu-metal, a well known and commercially available high-permeability material (having a composition of 77 weight percent nickel, 5 weight percent copper, 1.5 weight percent chromium, balance iron), commercially pure copper, and commercially pure aluminum, in a thickness of about ⅛ inch. Since mu-metal has a relatively large permanent magnetic moment and copper has a higher conductivity than aluminum, copper sheet in a thickness of ⅛ inch is the presently most preferred material for use in forming the shield 80.

As indicated, the shield 80 has an open end so that the subject may view the image on the CRT. Consequently, the shield 80 will necessarily permit the escape of magnetic field from its interior. The shield is used with the understanding that it is only partially effective, and with the further understanding that other magnetic field attenuation techniques such as the cancellation coils and filtering are usually necessary. It is therefore preferred to use all three techniques together. The cancellation coils and shielding reduce the unwanted magnetic field produced by the display as much as possible, and a large portion of the remaining field is removed with the filtering described previously. Removal of a portion of the unwanted magnetic field by cancellation coils and shielding improves the effectiveness of the filtering.

The present approach has been tested utilizing the preferred approach described above, without any cancellation coil set 70, and found satisfactory in reducing interference produced from the monitor. With the preferred apparatus using a comb-notch filter, a reduction was achieved of about 100:1 in the interference produced by the CRT, thereby permitting more effective study of the response magnetic field of the subject.

The approach of the invention provides a technique to obtain the responses of subjects to a variety of visual stimuli that are observed in the controlled, familiar setting of a CRT or other display, which as a result of operation generates magnetic interference. Although particular embodiments of the invention have been described in detail for purposes of illustration, various modifications may be made without departing from the spirit and scope of the invention. Accordingly, the invention is not to be limited except as by the appended claims.

What is claimed is:

1. Apparatus for performing biomagnetic measurements of visually stimulated responses in a subject, comprising:

means for detecting biomagnetic signals produced by a subject and having an output signal indicative of the biomagnetic signals;

means for producing a visual image responsive to an electrical signal, the means for producing being disposed for viewing by the subject and in sufficient proximity to the subject that magnetic interference emitted by the means for producing is detected by the means for detecting and becomes mixed with the output signal of the means for detecting; and means for reducing the effect of the magnetic interference produced by the means for producing on the output signal of the means for detecting.

2. The apparatus of claim 1, further including a magnetically shielded enclosure, and wherein the subject, the means for producing, and the means for detecting are placed within the magnetically shielded enclosure.

3. The apparatus of claim 1, wherein the means for reducing includes a filter on the output signal of the means for detecting that attenuates those frequencies in the output signal resulting from the electrical signal used to produce the visual image in the means for producing.

4. The apparatus of claim 3, wherein the electrical signal supplied to the means for producing includes a periodic synchronization signal, and the means for reducing filters the output signal of the means for detecting at the fundamental and the harmonic frequencies of the synchronization signal.

5. The apparatus of claim 3, wherein the filter comprises a comb-notch filter.

6. The apparatus of claim 3, wherein the filter comprises a digital filter.

7. The apparatus of claim 1, wherein the means for reducing includes a magnetic field cancellation coil set having means for nulling out at least a portion of the magnetic interference emitted by the means for producing.

8. The apparatus of claim 1, wherein the means for reducing includes a magnetic field shield around at least a portion of the means for producing.

9. Apparatus for performing biomagnetic measurements of visually stimulated responses in a subject, comprising:

a biomagnetometer having an output signal, the biomagnetometer being disposed to detect magnetic fields produced by a subject;

a signal generator that generates a repetitive electrical synchronization signal;

a display device responsive to the repetitive electrical synchronization signal received from the signal generator, the display device being disposed for viewing by the subject and sufficiently close to the subject that a magnetic field produced by the display device as a result of the repetitive synchronization signal is detected by the biomagnetometer;

magnetic shielding means at least partially surrounding the display device for reducing the portion of the magnetic field sensed by the biomagnetometer that is produced by the display device;

magnetic field cancellation means for cancelling at least a portion of the magnetic field produced by the display device;

a magnetically shielded enclosure in which the subject, the display device, the magnetic shielding means, the magnetic field cancellation means, and the biomagnetometer are located; and means for filtering from the output signal of the biomagnetometer those portions of the output signal resulting from the operation of the display device.

10. The apparatus of claim 9, wherein the means for filtering includes a comb-notch filter.

11. The apparatus of claim 9, wherein the means for filtering includes a digital filter.

12. The apparatus of claim 9, wherein the magnetic field cancellation means includes at least one adjustable coil set that emits a magnetic field to cancel out a portion of the magnetic field produced by the display device.

13. The apparatus of claim 9, wherein the magnetic shielding means includes a sheet of an electrically conducting material at least partially surrounding the display device.

14. A process for detecting biomagnetic signals resulting from visually induced responses in a subject, comprising the steps of:

providing a visual image to a subject on a display device that produces a magnetic field as it operates;

detecting the magnetic field produced by the subject responsive to the visual signal and the magnetic field produced by the display device as it operates, and generating an output signal indicative of the detected magnetic fields; and reducing the magnitude of those portions of the output signal resulting from the magnetic field produced by the display device.

15. The process of claim 14, wherein the step of reducing includes the step of placing a shield around the display device to reduce the magnetic field emitted by the display device.

16. The process of claim 14, wherein the step of reducing includes the step of cancelling at least a portion of the magnetic field emitted by the display device.

17. The process of claim 14, wherein the step of reducing includes the step of filtering those frequencies of the output signal resulting from the magnetic field produced by the display device.

18. The process of claim 17, wherein the display device include a cathode ray tube that produces a visual image responsive to a repetitive synchronization signal.

19. The process of claim 18, wherein the frequencies filtered in the step of filtering include those at the fundamental frequency of the synchronization signal.

20. The process of claim 17, wherein the step of filtering is accomplished by a comb-notch filter.

* * * * *